US012577221B2

(12) United States Patent
Tanaka et al.

(10) Patent No.: US 12,577,221 B2
(45) Date of Patent: Mar. 17, 2026

(54) CYCLOCARBONATE GROUP-CONTAINING (METH)ACRYLATE MONOMER AND POLYMER

(71) Applicant: NOF CORPORATION, Tokyo (JP)

(72) Inventors: Masahiro Tanaka, Kawasaki (JP); Akihiro Yamada, Amagasaki (JP); Tatsuya Aono, Amagasaki (JP); Kazuhiro Oda, Nishinomiya (JP)

(73) Assignee: NOF CORPORATION, Tokyo (JP)

( * ) Notice: Subject to any disclaimer, the term of this patent is extended or adjusted under 35 U.S.C. 154(b) by 811 days.

(21) Appl. No.: 17/790,330

(22) PCT Filed: Jan. 23, 2020

(86) PCT No.: PCT/JP2020/002241
§ 371 (c)(1),
(2) Date: Jun. 30, 2022

(87) PCT Pub. No.: WO2021/144996
PCT Pub. Date: Jul. 22, 2021

(65) Prior Publication Data

US 2023/0076090 A1 Mar. 9, 2023

(30) Foreign Application Priority Data

Jan. 15, 2020 (JP) ................................ 2020-004256

(51) Int. Cl.
*C07D 317/36* (2006.01)
*C08F 20/28* (2006.01)
*C08F 220/28* (2006.01)
*C08F 222/10* (2006.01)

(52) U.S. Cl.
CPC ........ *C07D 317/36* (2013.01); *C08F 220/283* (2020.02); *C08F 220/285* (2020.02); *C08F 222/102* (2020.02)

(58) Field of Classification Search
CPC ............... C07D 317/36; C08F 220/283; C08F 220/285; C08F 220/282; C08F 222/102; C08F 222/1063; C08F 20/28
See application file for complete search history.

(56) References Cited

U.S. PATENT DOCUMENTS

| | | | |
|---|---|---|---|
| 6,627,762 B1 | 9/2003 | Woods et al. |
| 2007/0106044 A1 | 5/2007 | Schmitt et al. |
| 2015/0329666 A1 | 11/2015 | Michaud et al. |
| 2016/0077431 A1 | 3/2016 | Nishimura et al. |
| 2021/0163439 A1 | 6/2021 | Treskow et al. |

FOREIGN PATENT DOCUMENTS

| | | | |
|---|---|---|---|
| CN | 102146071 A | 8/2011 |
| CN | 108299375 A | 7/2018 |
| DE | 3937116 A1 | 5/1991 |
| EP | 0 328 150 A2 | 8/1989 |
| EP | 0489203 A1 | 6/1992 |
| JP | 56-18938 A | 2/1981 |
| JP | 02-787 A | 1/1990 |
| JP | 03-2206 A | 1/1991 |
| JP | 05-202022 A | 8/1993 |
| JP | 2000-191604 A | 7/2000 |
| JP | 2011-32222 A | 2/2011 |
| JP | 2014-51456 A | 3/2014 |
| JP | 2014-105265 A | 6/2014 |
| JP | 2014-183833 A | 10/2014 |
| JP | 2016-074831 A | 5/2016 |
| JP | 2019-196446 A | 11/2019 |
| JP | 2020-19745 A | 2/2020 |
| WO | 2013/081157 A1 | 6/2013 |
| WO | 2019/238548 A1 | 12/2019 |

OTHER PUBLICATIONS

JP2014105265 machine translation, translation of JP 2014105265, 2014.*

(Continued)

*Primary Examiner* — Sun Jae Yoo
(74) *Attorney, Agent, or Firm* — Sughrue Mion, PLLC

(57) ABSTRACT

A method of producing a polymer, including a step of subjecting a monomer mixture to radical polymerization, the monomer mixture including a cyclocarbonate group-containing (meth)acrylate monomer (A) represented by the following formula (1) and di(meth)acrylate monomer (B) represented by the following formula (2), wherein a content of the di(meth)acrylate monomer (B) is 3 weight % or lower with respect to a total of a content of the monomer (A) and the content of the monomer (B), (1)

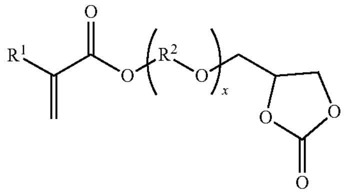

wherein $R^1$ represents hydrogen atom or methyl group, $R^2$ represents an alkyl group having a number of carbons of 2 to 10, and X is 0 or 1, (2)

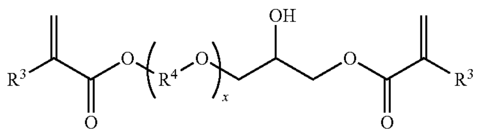

wherein $R^3$ represents hydrogen atom or methyl group, $R^4$ represents an alkyl group having a number of carbons of 2 to 10, and X is 0 or 1.

5 Claims, No Drawings

(56) References Cited

OTHER PUBLICATIONS

"(2-Oxo-1, 3-dioxolan-4-yl) methyl Methacrylate", Website of Tokyo Chemical Industry Co., Lt., [online], [retrieved on Mar. 11, 2020], internet:URL:https://www.tcichemicals.com/eshop/ja/ip/commodity/00553/, published date unknown (2 pages total).
Büttner et al., "Synthesis of Cyclic Carbonates from Epoxides and Carbon Dioxide by Using Bifunctional One-Component Phosphorus-Based Organocatalysts", ChemSusChem, vol. 8, No. 16, pp. 2655-2669, 2015 (15 pages total).
Werner et al., "Hydroxyl-Functionalized Imidazoles: Highly Active Additives for the Potassium Iodide-Catalyzed Synthesis of 1,3-Dioxolan~2-one Derivatives from Epoxides and Carbon Dioxide", ChemCatChem, vol. 6, No. 12, pp. 3493-3500, 2014 (8 pages total).
Aoyagi et al., "Remarkably Efficient Catalysts of Amidine Hydroiodides for the Synthesis of Cyclic Carbonates from Carbon Dioxide and Epoxides under Mild Conditions", Chemistry Letters, vo. 41, No. 3, pp. 240-241, 2012 (2 pages total).
Aoyagi et al., "Effective synthesis of cyclic carbonates from carbon dioxide and epoxides by phosphonium iodides as catalysts in alcoholic solvents", Tetrahedron Letters, vol. 54, No. 51, pp. 7031-7031, 2013 (4 pages total).
International Search Report dated Apr. 14, 2020 from the International Searching Authority in International Application No. PCT/JP2020/002241.
Office Action dated Nov. 10, 2021 from the Japanese Patent Office in JP Application No. 2018-146410.
Extended European Search Report dated Oct. 19, 2023 in Application No. 20914420.3.

* cited by examiner

CYCLOCARBONATE GROUP-CONTAINING (METH)ACRYLATE MONOMER AND POLYMER

CROSS REFERENCE TO RELATED APPLICATIONS

This application is a National Stage of International Application No. PCT/JP2020/002241 filed on Jan. 23, 2020, claiming priority based on Japanese Patent Application No. 2020-004256 filed on Jan. 15, 2020.

TECHNICAL FIELD

The present invention is related to a cyclocarbonate group-containing (meth)acrylate monomer, and to the cyclocarbonate group-containing (meth)acrylate monomer and a polymer containing the same whose thickening over time is suppressed and which is applicable to applications such as a paint or the like stably for a long time.

BACKGROUND ARTS

Cyclocarbonate group generally has characteristics such as high polarity, high dielectric constant and high solubility with high polymers, and is applicable to various kinds of application thanks to the characteristic structure. Particularly in the case of a compound having cyclocarbonate group and (meth)acryloyl group, it may be polymerized with another monomer or oligomer to obtain a polymer to which cyclocarbonate group is introduced. The polymer, obtained by applying such cyclocarbonate group-containing (meth)acrylate monomer, may be used, for example, film and molding materials, sealing agents, paints, adhesive agents, and various kinds of binders.

The cyclocarbonate group-containing (meth)acrylate monomer can be usually obtained by effecting carbon dioxide on an epoxy compound. It is reported the methods of obtaining the monomer at a high yield, in patent documents 1 and 2. The cyclocarbonate group-containing (meth)acrylates described in these prior documents can be applied for synthesis of a polymer, so that the polymer having cyclocarbonate group at the side branch can be obtained. Such polymer is excellent in various kinds of properties such as transparency and viscosity and can be applied without a problem, as reported in patent document 3.

PRIOR TECHNICAL DOCUMENTS

Patent Documents (Patent document 1) Japanese Patent Publication No. 1993-202022A
(Patent document 2) Japanese Patent Publication No. 2011-032222A
(Patent document 3) Japanese Patent Publication No. 2014-105265A

SUMMARY OF THE INVENTION

Object to be Solved by the Invention

Recently, particularly in applications of a paint and ink, it is necessary to control the viscosity of the paint or ink extremely precisely, for attending the improvement of printing technique such as improvement of image quality or increase of printing speed, objects having complex shapes and high design quality such as blending of various kinds of colors. However, according to such applications, in the case that the polymer having cyclocarbonate group on the side branch obtained by the prior method described in each of patent documents 1 to 3 was applied, the viscosity may be slightly increased during the use under severe condition and storage over a long period of time, so that faint may possibly be generated during the printing.

Thus, even in the case of the polymer including cyclocarbonate group-containing monomer which can be obtained at a high yield, it is demanded the characteristics that the change of viscosity over time is suppressed to alleviate the possible defects such as the faint generated during the printing.

In the case that a cyclocarbonate group-containing (meth) acrylate monomer is made into the polymer used for a paint or the like, an object of the present invention is to provide the cyclocarbonate group-containing (meth)acrylate monomer, and the polymer containing the same, in which the increase of the viscosity over time is suppressed and usable stably for a long period of time.

Solution for the Object

As the inventors have extensively researched for solving the object described above, according to the reports known until now relating to the cyclocarbonate group-containing (meth)acrylate monomer, although it may be referred to epoxy compounds having various kinds of (meth)acrylate groups as raw materials for the monomer, it has not been investigated the content of di(meth)acrylate monomer contained in a certain amount as a byproduct.

Then, as it is investigated on the content of the di(meth) acrylate monomer, in the case that it is polymerized to produce a polymer used in applications such as a paint, it is found that the increase of the viscosity over time is suppressed and it can be stably used in applications such as a paint or the like for a long period of time.

That is, the present invention provides the following (1) and (2).

(1) A cyclocarbonate group-containing (meth)acrylate monomer (A) represented by a formula (1) as follows, wherein a content of a di(meth)acrylate monomer (B) represented by a formula (2) as follows is 3 weight % or lower.

(1)

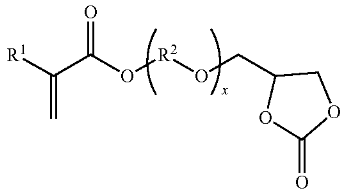

(In the formula (1),
$R^1$ represents hydrogen atom or methyl group,
$R^2$ represents an alkyl group having a number of 2 to 10 of carbon atoms, and
X is 0 or 1.)

(2)

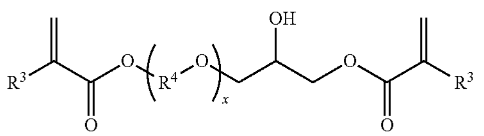

(In the formula (2), $R^3$ represents hydrogen atom or methyl group, $R^4$ represents an alkyl group having a number of 2 to 10 of carbon atoms, and X is 0 or 1.)

(2) A polymer comprising:

the cyclocarbonate group-containing (meth) acrylate monomer (A) of (1) in a mass ratio of 1 to 100 mass %, wherein a mass ratio of another monomer (C) capable of copolymerization with said monomer (A) is 0 to 99 mass %.

Effect of the Invention

The compound of the present invention is characterized by that the content of the di(meth)acrylate monomer is lower than that of the prior art. The cyclocarbonate group-containing (meth)acrylate monomer is applied as a monomer or polymerized into a polymer, which is applied for a paint or the like, so that the increase of the viscosity over time is suppressed and it can be used in applications such as a paint or the like stably for a long period of time.

EMBODIMENTS FOR CARRYING OUT THE INVENTION

Embodiments for carrying out the present invention will be described further in detail below.

[(A) Cyclocarbonate Group-Containing (meth)acrylate Monomer]

The cyclocarbonate group-containing (meth)acrylate monomer (A) of the present invention is shown in the following formula (1).

(1)

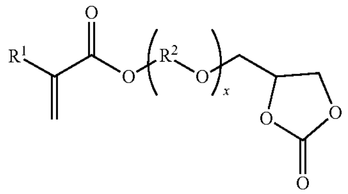

The cyclocarbonate group-containing (meth)acrylate monomer (A) of the present invention is a monomer characterized by including one cyclocarbonate group and one (meth)acryloyl group in the single molecule.

In the formula (1), $R^2$ indicates an alkyl group having a number of carbons of 2 to 10. As $R^2$ is the alkyl group having a number of carbons of 2 to 10, the reactivity in the synthesis of the polymer is good, so that it is possible to obtain the polymer whose monomer residue is small in quantity. Among them, the number of carbons of $R^2$ may preferably be 2 to 4, and the number of carbons of $R^2$ may more preferably be 2.

In the formula (1), X has a value of 0 or 1. Among them, X may preferably be 0. As X is 0 or 1, the reactivity in the synthesis of the polymer is good, so that it is possible to obtain the polymer having a small content of the monomer residue.

[Di(meth)acrylate Monomer (B)]

Di(meth)acrylate monomer (B) is represented by the following formula (B).

(2)

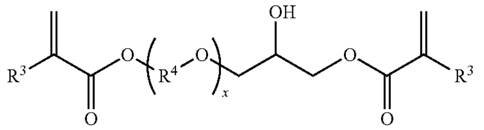

(In the formula (2), $R^3$ represents hydrogen atom or methyl group, $R^4$ represent an alkyl group having a number of carbons of 2 to 10, X is 0 or 1.)

Di(meth)acrylate monomer (B) is contained in the cyclocarbonate group-containing (meth)acrylate monomer (A) as a byproduct. Further, the structure of the di(meth)acrylate monomer (B) is changed by what is selected as a monomer in starting materials. For example, in the case that glycidyl (meth)acrylate is applied as the raw material, glycerin di(meth)acrylate is generated. The structure and the content of the thus generated di(meth)acrylate monomer (B) can be identified by appropriate methods such as gas chromatography, high-speed liquid chromatography, nuclear magnetic resonance or the like.

As the di(meth)acrylate monomer (B) is generated as the byproduct when the cyclocarbonate group-containing (meth)acrylate monomer (A) is produced, $R^4$ represents an alkyl group having a number of carbon atoms of 2 to 10. Among them, the number of carbons of $R^4$ may preferably be 2 to 4, and may most preferably be 2.

In the formula (2), X has a value of 0 or 1. Among them, X is preferably 0. In the case that X has such value, the reactivity in the synthesis of the polymer is good so that it is possible to obtain the polymer whose monomer residue is small in quantity.

(Content of di(meth)acrylate Monomer (B))

In the case that 100 mass % is assigned to the content of the cyclocarbonate group-containing acrylate monomer (A) represented by the formula (1), the content of the di(meth) acrylate monomer (B) represented by the formula (2) contained in the monomer (A) is made 3 mass % or lower, is more preferably 1.5 mass % or lower and is most preferably 1.0 mass % or lower. If it is contained in an amount higher than 3 mass %, during the polymer synthesis applying the cyclocarbonate group-containing (meth)acrylate monomer of the invention, the molecular weight is increased, the viscosity is increased and gelling reaction takes place due to storage.

Further, in the case that 100 mass % is assigned to the content of the cyclocarbonate group-containing (meth)acrylate monomer (A), the lower limit of the di(meth)acrylate monomer (B) contained in the monomer (A) is not particularly defined, and may be 0 mass %. However, on the viewpoint of suppression of increase of the viscosity over time and properties of the hardened film, the content of the di(meth)acrylate monomer (B) contained in the monomer (A) may preferably be 0.1 mass % or higher, more preferably be 0.3 mass % or higher and most preferably be 0.5 mass % or higher.

[Method of Producing Cyclocarbonate Group-Containing (meth)acrylate Monomer]

The cyclocarbonate group-containing (meth)acrylate monomer (A) can be obtained by blowing carbon dioxide at about 0.05 to 0.3 MPa onto an epoxy compound having each of various kinds of (meth)acryloyl groups as a starting material, to perform the reaction of them. At this time, various kinds of monomers can be selected as the epoxy compounds having (meth)acryloyl groups. However, on the viewpoints of a low viscosity, of a short time duration required for the reaction, and of a low color phase and good transparency of the thus obtained cyclocarbonate group-containing (meth)acrylate monomer (A), glycidyl (meth) acrylate, or 4-hydroxy butyl (meth)acrylate glycidyl ether may preferably be applied, and glycidyl (meth) acrylate may more preferably be applied.

According to the present invention, carbon dioxide is acted upon epoxy group, which is converted to cyclocarbonate group. As the method of introducing carbon dioxide into the reaction system, various kinds of blowing methods under pressurized condition may be selected. At this time, the pressure and temperature are controlled in predetermined ranges so that the yield of the target product can be improved and the content of the byproduct can be suppressed at a low value. The pressure in this case is 0.05 to 0.3 MPaG and is preferably 0.1 to 0.2 MPaG. When the pressure is set at a high value exceeding 0.3 MPaG, the yield of the cyclocarbonate body is not increased and side reaction is facilitated, so that the content of the di(meth(acrylate monomer (B) generated as the byproduct exceeds 3 mass %.

The reaction temperature during the synthesis is in a range of 40 to 70° C. and preferably in a range of 50 to 60° C., depending on the conditions of the pressure or solvent. In the case it is lower than 40° C., the time duration required for the reaction is too long and unreacted raw material tends to be left. Further, the coloration tends to occur. On the other hand, it exceeds 70° C., too much di(meth)acrylate monomer (B) is contained and defects such as gel formation tend to occur in the polymerization. Further, the coloration tends to occur.

[(C) Another Monomer]

The polymer of the present invention can be obtained by polymerizing the monomer (A) in which the mass of the monomer (B) described above is 3 mass % or lower. However, the polymer of the present invention may contain another monomer (C). The monomer (C) is not particularly limited as far as the monomer can be copolymerized with the monomer (A), it may contain one kind or two or more kinds, and may preferably be (meth)acrylate ester monomer or aromatic vinyl compound.

The (meth)acrylate ester monomer may be, for example, methyl (meth)acrylate, ethyl (meth)acrylate, propyl (meth) acrylate, butyl (meth)acrylate, pentyl (meth)acrylate, hexyl (meth)acrylate, cyclohexyl (meth)acrylate, heptyl (meth) acrylate, octyl (meth)acrylate, 2-ethyl hexyl (meth)acrylate, nonyl (meth)acrylate, decyl (meth)acrylate, dodecyl (meth) acrylate, phenyl (meth)acrylate, benzyl (meth)acrylate, 2-methoxyethyl (meth)acrylate, 3-methoxybutyl (meth) acrylate, 2-hydroxyethyl (meth)acrylate, glyceryl (meth) acrylate, hydroxypropyl (meth)acrylate, hydroxy butyl (meth)acrylate, stearyl (meth)acrylate, ethylene oxide adduct of (meth)acrylic acid or the like. The (meth)acrylate ester may preferably be methyl (meth)acrylate, ethyl (meth) acrylate, propyl (meth)acrylate, butyl (meth) acrylate, cyclohexyl (meth)acrylate, 2-ethylhexyl (meth)acrylate or benzyl (meth)acrylate, and it may more preferably be methyl (meth) acrylate, ethyl (meth)acrylate, propyl (meth)acrylate, butyl (meth)acrylate, cyclohexyl (meth)acrylate, or 2-ethylhexyl (meth)acrylate.

The aromatic vinyl compound may be styrene, α-methylstyrene, p-methylstyrene, m-methylstyrene, o-methylstyrene, p-ethylstyrene, m-ethylstyrene, o-ethylstyrene, t-butylstyrene, chlorostyrene, hydroxystyrene, t-butoxystyrene, vinyltoluene, vinylnaphthalene or the like, and may preferably be styrene.

The polymer of the present invention may be a polymer obtained by polymerizing the monomer (A), in which a mass of the monomer (B) is 3 mass % or lower. Alternatively, the polymer of the present invention may be a polymer obtained by copolymerizing the monomer (A), in which a mass of the monomer (B) is 3 mass % or lower, with the another monomer (C).

According to a preferred embodiment, the ratio of copolymerization of structural units derived from the monomer (A) in structural units constituting the polymer is 1 to 100 mass %, preferably 5 to 80 mass %, more preferably 10 to 60 mass %, and most preferably 15 to 40 mass %, provided that 100 mass % is assigned to a total of the masses of the monomers before the polymerization.

Further, the ratio of copolymerization of structural units derived from the another monomer (C) in the structural units constituting the polymer of the present invention is 0 to 99 mass %, preferably 20 to 95 mass %, more preferably 40 to 90 mass %, and most preferably 60 to 85 mass %, provided that the total of masses of the monomers before polymerization is 100 mass %.

[Polymer]

The weight average molecular weight of the polymer of the present invention can be calculated by gel permeation chromatography (GPC) as a converted value in polystyrene, is preferably 3,000 to 1,000,000, is more preferably 10,000 to 800,000 and most preferably 50,000 to 300,000. As the weight average molecular weight of the polymer is too low, the film strength in the case of a paint may be lowered, and as the weight average molecular weight is too high, the solubility in a solvent or viscosity of the solution may become too high so that the workability may be deteriorated.

Specifically, in the case that the polymer is synthesized from the cyclocarbonate group-containing (meth)acrylate monomer of the present invention, the ratio (d/c) of the viscosity (d) after the polymer is stored for 1 month at 40° C. with respect to the viscosity (c) of the polymer direct after the synthesis is 1.00 or higher, preferably 1.20 or lower, more preferably 1.15 or lower, particularly preferably 1.05 or lower and most preferably 1.02 or lower.

[Method of Producing Polymer]

Then, it will be descried the method of producing the polymer of the present invention.

The polymer of the present invention can be obtained by subjecting monomer mixture, containing at least the monomer (A) which may contain the monomer (B) and optionally the monomer (C), to radical polymerization. The polymerization can be performed by a known method. For example, solution polymerization, suspension polymerization, emulsion polymerization or the like are listed, and the solution polymerization or emulsion polymerization is preferred on the viewpoint of ease of adjusting the weight average molecular weight of the copolymer in the range described above.

Known polymerization initiators may be applied. For example, it may be listed an organic peroxide such as 1,1,3,3-tetramethylbutyl peroxy-2-ethyl hexanoate or the like, an azo-based polymerization initiator such as 2,2'-azoisobutyronitrile or the like. One kind or two or more kinds of the polymerization initiators may be applied.

The amount of the applied polymerization initiator may be appropriately selected depending on the combination of the monomers, reaction condition or the like.

Further, when the polymerization initiator is charged, for example, the whole amount may be charged in batch, or a part is charged in batch and the remainder may be added dropwise, or the whole amount may be added dropwise. Further, the polymerization initiator may preferably be added dropwise with the monomers so that the control of the reaction is facilitated, and the polymerization initiator may preferably be added after the dropwise addition of the monomers so that the residual monomers can be reduced.

As a solvent for the polymerization applied for use in the solution polymerization, it may be applied a solvent in which the monomers and polymerization initiator are soluble. Specifically, methanol, ethanol, 1-propanol, acetone, methyl ethyl ketone, propylene glycol monomethyl ether, N, N-dimethyl formamide or the like may be listed.

The concentration of the monomer (total amount) with respect to the polymerization solvent may preferably be 10 to 60 mass % and more preferably be 20 to 50 mass %. In the case that the concentration of the monomer mixture is too low, the monomers tend to remain so that the molecular weight of the thus obtained copolymer may possibly be lowered, and in the case that the concentration of the monomer is too high, the control of heat generation may possibly become difficult.

When the monomer is charged, for example, the whole amount may be charged in batch, or a part may be charged in batch and the remainder may be added dropwise, or the whole amount may be added dropwise. On the viewpoint of facilitating heat generation, a part may preferably be added in batch and the remainder may be added dropwise, or the whole amount may preferably be added dropwise.

The polymerization temperature is dependent on the kind of the polymerization solvent and 50 to 110° C., for example. The time duration of the polymerization is dependent on the kind of the polymerization initiator and polymerization temperature, and for example, in the case that di(4-t-butylcyclohexyl) peroxydicarbonate is applied as the polymerization initiator and the polymerization is performed at a polymerization temperature of 70° C., the time duration for the polymerization is suitably about 6 hours.

The polymerization reaction described above is performed to obtain the polymer of the present invention. The thus obtained polymer may be applied as itself or isolated by performing filtration or purification on the reaction solution after the polymerization reaction.

EXAMPLES

The present invention will be described further in detail referring to the inventive and comparative examples below.

(Experiment 1)

[Evaluation Method]

(Quantitative Analysis of Components)

It was performed the quantitative analysis of components of the cyclocarbonate group-containing (meth)acrylate monomer (A) and di(meth)acrylate monomer (B), by means of a gas chromatography (GC) under the following conditions. Based on the ratio of area of the peak (A) and the area of the peak (B), the respective yields of the cyclocarbonate group-containing (meth)acrylate monomer (A) and di(meth) acrylate monomer (B) were calculated. The yield of (A) is defined as the content (mass %) of (A) and the yield of (B) is defined as the content (mass %) of (B).

(Mass ratio (mass %) of monomer (B) contained in monomer (A)=Yield (content: mass %) of monomer (B)/[Yield (content: mass %) of monomer (A)+yield (content: mass %) of monomer (B)]=Area of peak of monomer (B)/[area of peak of monomer (A)+area of peak of monomer (B)]

Further, conversion rate was calculated according to the following formula.

Conversion rate (%)="(area of (cyclocarbonate group-containing (meth)acrylate monomer(A)/(total of areas of all peaks)"×100

(Condition of GC)

System: GC-2014 (supplied by Shimadzu corporation)
Column: DB-1
Injection temperature: 200° C.
Temperature of detector: 250° C.
Temperature ascending profile: Temperature is held at 40° C. for 10 minutes.→Temperature is increased at 10° C. /minute.→Temperature in increased to and then held at 250° C.
Injection amount: 1 μL
Detector: FID range 1
Carrier gas: helium, 70 kPa
Split ratio: 1/50
Quantifying method: Internal standard method (Biphenyl is used)

(Polymerization Test)

The thus obtained polymerizing composition was used to perform the polymerization under the following conditions.

Blended composition: Polymerizing composition 50 g
Methyl methacrylate 50 g
Initiator: 2,2'-azo bis(2,4-dimethyl valeronitrile) (Product name "V-65" (supplied by Wako Pure chemical Industries Ltd.) 0.4 g
Solvent: Isopropanol 150 g
Reaction temperature: 75° C.
Rection time: 3 hours (Evaluation of Viscosity)

The thus obtained polymer solution was subjected to the evaluation of viscosity. Specifically, the viscosity (c) directly after the synthesis of the polymer solution and viscosity after storing in a constant temperature bath at 40° C. over 1 month were measured. The ratio of the viscosities was represented by "viscosity after storage/viscosity directly after synthesis (d/c), and evaluated according to the following standard.

○: Ratio of viscosities (die) is 1.0 or higher and less than 1.1.
Δ: Ratio of viscosities (die) is 1.1 or higher and less than 1.3.
x: Ratio of viscosities (d/c) is 1.3 or higher, or not measurable.

The cyclocarbonate group-containing (meth)acrylate monomers of the respective examples were synthesized as follows.

Inventive Example 1-1

1,000 parts of "BLEMMER GH" (glycidyl methacrylate), 50 parts of sodium iodide and 0.5 parts of methoxy hydroquinone were charged as raw materials in an autoclave equipped with a supply tube for carbon dioxide, agitator and thermometer. While the temperature in the system was adjusted at 50° C., carbon dioxide was intermittently blown into the system from a carbon dioxide gas bombe with the inside of the system maintained at 0.2 MPa to perform the reaction under agitation over 8 hours. After it was cooled to room temperature, 300 parts of ion exchange water was charged, agitated well and stood still for a while so that an organic phase and aqueous phase were separated, followed by the removal of the aqueous phase. The operation was reacted four times to remove sodium iodide. Thereafter, the organic phase was subjected to dehydration at 70° C. over 2 hours under reduced pressure to obtain the target monomer.

Inventive Example 1-2

1,000 parts of "BLEMMER GH" (glycidyl methacrylate), 50 parts of lithium bromide, 53.5 parts of diazabicyclo undecene and 0.5 parts of methoxy hydroquinone were charged in an autoclave equipped with a carbon dioxide supply tube, agitator and thermometer. While the temperature in the system was adjusted at 60° C., carbon dioxide was intermittently blown from a carbon dioxide gas bombe with the inside of the system maintained at 0.05 MPa to perform the reaction under agitation over 8 hours. After it was cooled to room temperature, 300 parts of ion exchange water was charged, agitated well and stood still for a while so that an organic phase and aqueous phase were separated, followed by the removal of the aqueous phase. The operation was repeated four times to remove sodium iodide. Thereafter, the organic phase was dehydrated at 70° C. over 2 hours under reduced pressure to obtain the target monomer.

Inventive Example 1-3

1,000 parts of "BLMMER GH" (glycidyl methacrylate), 50 parts of lithium bromide, 53.5 parts of diazabicyclo undecene, 0.5 parts of methoxy hydroquinone and 500 parts of dimethyl formamide were charged into an autoclave equipped with a carbon dioxide supply tube, agitator and thermometer. While a blow valve was opened and the temperature in the system was adjusted at 50° C., carbon dioxide was intermittently blown from a carbon dioxide gas bombe with the inside of the system maintained at 0.05 MPa to perform the reaction under agitation over 8 hours. After it was cooled to room temperature, 300 parts of ion exchange water was charged, agitated well and stood still for a while so that an organic phase and aqueous phase were separated, followed by the removal of the aqueous phase. The operation was repeated four times to remove sodium iodide. Thereafter, the organic phase was dehydrated at 70° C. over 2 hours under reduced pressure to obtain the target monomer.

Inventive Example 1-4

1,000 parts of 4-hydroxybutyl acrylate glycidyl ether, 50 parts of sodium iodide and 0.5 parts of methoxy hydroquinone were charged into an autoclave equipped with a carbon dioxide supply tube, agitator and thermometer. While the temperature in the system was adjusted at 50° C., carbon dioxide was intermittently blown from a carbon dioxide gas bombe with the inside of the system maintained at 0.08 MPa to perform the reaction upon stirring over 8 hours. After the system was cooled to room temperature, 300 parts of ion exchange water was charged, agitated well and stood still for a while so that an organic phase and aqueous phase were separated, followed by the removal of the aqueous phase. The operation was repeated four times to remove sodium iodide. Thereafter, the organic phase was dehydrated at 70° C. under reduced pressure over 2 hours to obtain the target monomer.

Inventive Example 1-5

1,000 parts of 4-hydroxy butyl acrylate glycidyl ether, 50 parts of sodium iodide and 0.5 parts of methoxy hydroquinone were charged into an autoclave equipped with a carbon dioxide supply tube, agitator and thermometer. While the temperature in the system was adjusted at 50° C., carbon dioxide was intermittently blown from a carbon dioxide gas bombe with the inside of the system maintained at 0.2 MPa to perform the reaction upon stirring over 8 hours. After the system was cooled to room temperature, 300 parts of ion exchange water was charged, agitated well, and stood still for a while so that an organic phase and aqueous phase were separated, followed by the removal of the aqueous phase. The operation was repeated four times to remove sodium iodide. Thereafter, the organic phase was dehydrated at 70° C. under reduced pressure over 2 hours to obtain the target monomer.

Comparative Example 1-1

1,000 parts of "BLEMMER GH" (glycidyl methacrylate), 50 parts of sodium iodide and 0.5 parts of methoxy hydroquinone were charged into an autoclave equipped with a carbon dioxide supply tube, agitator and thermometer. While the temperature in the system was adjusted at 75° C., carbon dioxide was intermittently blown from a balloon filled with carbon dioxide gas to perform the reaction upon stirring over 15 hours. After the system was cooled to room temperature, 300 parts of ion exchange water was charged, agitated well and stood still for a while so that an organic phase and aqueous phase were separated, followed by the separation of the aqueous phase. The operation was repeated four times to remove sodium iodide. Thereafter, the organic phase was dehydrated at 70° C. under reduced pressure over 2 hours to obtain the target monomer.

TABLE 1

| | | Inventive Example 1-1 | Inventive Example 1-2 | Inventive Example 1-3 | Inventive Example 1-4 | Comparative Example 1-1 | Comparative Example 1-2 |
|---|---|---|---|---|---|---|---|
| Content (%) | cyclocarbonate group-containing (meth)acrylate monomer (A) | 98.5 | 98.7 | 99.2 | 99.6 | 97.3 | 93.8 |
| | Di(meth)acylate monomer (B) | 1.5 | 1.3 | 0.8 | 0.4 | 2.7 | 6.2 |
| Conversion rate (%) | | 98.4 | 96.7 | 98.8 | 95.2 | 96.6 | 93.5 |
| Viscosity (c) (Pa · s/25° C.) directly after systhesis | | 30 | 32 | 28 | 33 | 33 | 45 |

TABLE 1-continued

| | Inventive Example 1-1 | Inventive Example 1-2 | Inventive Example 1-3 | Inventive Example 1-4 | Comparative Example 1-1 | Comparative Example 1-2 |
|---|---|---|---|---|---|---|
| Viscosity (d) (Pa · s/25° C.) after satorage at 40° C. for 1 month | 31 | 32 | 28 | 34 | 38 | gellation |
| Ratio (d/c) of viscosities | 1.03 | 1.00 | 1.00 | 1.03 | 1.15 | — |

As can be seen from the results shown in table 1, according to the inventive examples 1-1 to 1-5 of the present invention, it could be obtained monomers excellent in the respective properties.

Further, according to the comparative example 1-1, as the content of the dimethacrylate exceeds the range of the present invention, the viscosity of the polymer directly after the synthesis was relatively high and the gelation occurred during storage for a long time, so that the measurement of the ratio of the viscosities was impossible.

(Experiment 2)

[Analysis of Monomer (A)]

(Quantitative Analysis of Components)

It was performed the quantitative analysis of the cyclocarbonate group-containing (meth)acrylate monomer (A) and di(meth)acrylate monomer (B) under the following conditions, by means of gas chromatography (GC). Based on the ratio of the areas of the peak (A) and of peak (B), the contents of the cyclocarbonate group-containing (meth) acrylate monomer (A) and di(meth)acrylate monomer (B) were calculated.

Conditions of GC

System: "GC-2014" (supplied by Shimadzu corporation)

Colum: DB-1

Injection temperature: 200° C.

Detector temperature: 250° C.

Temperature ascending profile: Temperature was held at 40° C. for 10 minutes→Temperature was increased at 10° C./minutes→Temperature was increased to and then held at 250° C.

Injected amount: 1 μL

Detector: FID range 1

Carrier gas: helium 70 kPa

Split ratio: 1/50

[Examples of Synthesis]

The cyclocarbonate group-containing (meth)acrylate monomers of the respective examples were synthesized as follows.

(Synthesis of Monomer A1)

1,000 parts of "BLEMMER GH" (glycidyl methacrylate), 50 parts of lithium bromide, 53.5 parts of diazabicyclo undecene, 0.5 parts of methoxy hydroquinone and 500 parts of dimethyl formamide were charged in an autoclave equipped with a carbon dioxide supply tube, agitator and thermometer. While a blow valve was opened and the temperature in the system was adjusted at 50° C., carbon dioxide was intermittently blown from a carbon dioxide gas bombe with the inside of the system maintained at 0.05 MPa to perform the reaction upon stirring over 8 hours. After it was cooled to room temperature, 300 parts of ion exchange water was charged, agitated well and stood still for a while so that an organic phase and aqueous phase were separated, followed by the removal of the aqueous phase. The operation was repeated four times to remove sodium iodide. Thereafter, the organic phase was dehydrated at 70° C. under reduced pressure over 2 hours to obtain the target monomer A1. The purity of the thus obtained monomer A1 was 99.2 mass % and the amount of the di(meth)acrylate monomer was 0.8 mass %.

(Synthesis of Monomer A2)

1,000 parts of 4-hydroxy butyl acrylate glycidyl ether, 50 parts of sodium iodide and 0.5 parts of methoxy hydroquinone were charged into an autoclave equipped with a carbon dioxide supply tube, agitator and thermometer. While the temperature in the system was adjusted at 50° C., carbon dioxide was intermittently blown from a carbon dioxide gas bombe with the inside of the system maintained at 0.08 MPa to perform the reaction upon stirring over 8 hours. After it was cooled to room temperature, 300 parts of ion exchange water was charged, agitated well and stood still for a while so that an organic phase and aqueous phase were separated, followed by the removal of the aqueous phase. The operation was repeated four times to remove sodium iodide. Thereafter, the organic phase was dehydrated at 70° C. under reduced pressure over 2 hours to obtain the target monomer A2. The purity of the thus obtained monomer A2 was 99.6 mass %, and the amount of the di(meth)acrylate monomer was 0.4 mass %.

(Synthesis of Monomer A3)

1,000 parts of "BLEMMER GH" (glycidyl methacrylate), 50 parts of sodium iodide and 0.5 parts of methoxy hydroquinone were charged into an autoclave equipped with a carbon dioxide supply tube, agitator and thermometer. While the temperature in the system was adjusted to 90° C., carbon dioxide was intermittently blown from a balloon filled with carbon dioxide gas to perform the reaction upon stirring over 8 hours. After it was cooled to room temperature, 300 parts of ion exchange water was charged, agitated well and stood still for a while so that an organic phase and aqueous phase were separated, followed by the removal of the aqueous phase. The operation was repeated four times to remove sodium iodide. Thereafter, the organic phase was dehydrated at 70° C. under reduced pressure over 2 hours to obtain the target monomer A3. The purity of the thus obtained monomer A3 was 93.8 mass %, and the amount of the di(meth) acrylate monomer was 6.2 mass %.

Inventive Example 2-1

350 g of propylene glycol monomethyl ether was charged into 1 liter separable flask equipped with an agitator, thermometer, cooler, dropping funnel and nitrogen supply tube, and the inside of the flask was replaced with nitrogen to provide nitrogen atmosphere. Monomer solution was prepared by mixing 80.0 g of normal butyl methacrylate (supplied by Mitsubishi Gas chemical Company Inc.), 80.0 g of styrene (supplied by NS Styrene Monomer Co. Ltd.), 40.0 g of monomer A1 and 60 g of propylene glycol monomethyl ether, and polymerization initiator mixture was prepared by mixing 50 g of propylene glycol monomethyl ether and 2.0 g of 2,2'-azobis (2,4-dimethyl valeronitrile) (product name: "V-65" (supplied by Wako Pure Chemical Industries, Ltd.).

The inside of a reaction container was elevated to 75° C., and the monomer solution and polymerization initiator solution were added dropwise over 3 hours, respectively, at the same time. Thereafter, the reaction was performed at 75° C. for 3 hours to obtain propylene glycol monomethyl ether solution of the copolymer Pl. The solid content of the thus obtained solution was 30.1%.

Inventive Example 2-2

The copolymer P2 was obtained according to the same procedure as that of the inventive example 1-1, except that the monomer solution was changed to contain 50.0 g of normal butyl methacrylate, 60.0 g of styrene, 90.0 g of the monomer A1 and 60 g of propylene glycol monomethyl ether, and that the amount of 2,2'-azobis (2,4-dimethyl valeronitrile) was changed to 4.0 g. The solid content of the thus obtained solution was 30.3%.

Inventive Example 2-3

The copolymer P3 was obtained according to the same procedure as that of the inventive example 1-1, except that the monomer solution was changed to contain 70.0 g of normal butyl methacrylate, 130.0 g of the monomer A1 and 60 g of propylene glycol monomethyl ether, and that the amount of 2,2'-azobis (2,4-dimethyl valeronitrile) was changed to 8.0 g. The solid content of the thus obtained solution was 29.9%.

Inventive Example 2-4

The copolymer P4 was obtained according to the same procedure as that of the inventive example 1-1, except that the monomer solution was changed to contain 80.0 g of normal butyl methacrylate, 30.0 g of styrene, 90.0 g of the monomer A2 and 60 g of propylene glycol monomethyl ether and that the amount of 2,2'-azobis (2,4-dimethyl valeronitrile) was changed to 4.0 g. The solid content of the thus obtained solution was 30.4%.

Comparative Example 2-1

The copolymer P5 was obtained according to the same procedure as that of the inventive example 1-1, except that the monomer solution was changed to contain 80.0 g of normal butyl methacrylate, 80.0 g of styrene, 40.0 g of the monomer A3 and 60 g of propylene glycol monomethyl ether. The thus obtained solution had a solid content of 30.2%.

Comparative Example 2-2

The copolymer P6 was synthesized according to the same procedure as that of the inventive example 1-1, except that the monomer solution was changed to contain 80.0 g of normal butyl methacrylate, 20.0 g of styrene, 100.0 g of the monomer A3 and 60 g of propylene glycol monomethyl ether. Then, gelation occurred during the polymerization.

(Analysis of Copolymer)

(Weight Average Molecular Weight (Mw) of Polymer)

It was calculated under the following conditions by gal permeation chromatography (GPC).

GPC system: "HLC-8220" supplied by TOSOH corporation

Column: "Shodex KF-805L" supplied by Showa Denko Co. Ltd.,

Solvent: Tetrahydrofuran

Standard: Polystyrene (Solid Content of Polymer Solution)

1 g of the polymer solution was weighed in an aluminum pan and dried in a vacuum drier at 120° C. over 30 minutes. The solid content was calculated based on the weights before and after the drying.

[Method of Evaluation]

(Evaluation of Viscosity)

The thus obtained polymer solution was subjected to evaluation of viscosity. Specifically, the viscosity (c) directly after the synthesis of the polymer solution and viscosity (d) after the storage at 40° C. in a constant temperature bath over 1 month were measured. The ratio of the viscosities was represented by "viscosity after the storage/viscosity directly after the synthesis (d/c)" and evaluated based on the following standard.

⊙: The ratio (d/c) of the viscosities is 1.0 or higher and less than 1.02

○: The ratio (d/c) of the viscosities is 1.02 or higher and less than 1.1

Δ: The ratio (d/c) of the viscosities is 1.1 or higher and less than 1.3 x: The ratio (d/c) of the viscosities is 1.3 or higher, or is not measurable.

(Evaluation of Hardness of Hardened Film)

3,3-bipiperidine was added to 10 g of the polymer solution in an amount so that the molar amount of amino group is equivalent with that of the cyclocarbonate group in the polymer, to obtain uniform solution. It was applied on a glass substrate and the solvent was removed by vacuum drying. It was contained in a constant temperature bath maintained at 80° C. and heated for 3 hours to obtain a hardened film having a thickness of 5 μm.

The pencil hardness of the thus obtained hardened film was evaluated based on JIS K5600.

(Evaluation of Adhesion of Hardened Film)

3,3'-bipiperidine was added to 10 g of the polymer solution in an amount so that the molar amount of amino group is equivalent with that of the cyclocarbonate group in the polymer, to obtain uniform solution. It was applied on a glass substrate and the solvent was removed by vacuum drying. It was contained at 80° C. in a constant temperature bath and heated for 3 hours to obtain a hardened film having a thickness of 5 μm.

100 squares of cuttings were formed in the thus obtained hardened film, "Scotch tape" (trade mark; supplied by NICHIBAN CO. Ltd.) was adhered, the "Scotch tape" was peeled off and the adhesion was evaluated based on the number of the squares and appearance. It was evaluated as "○" in the case peeled squares were not observed, evaluated as "Δ" in the case that the peeled squares were not observed and broken squares were observed, and evaluated as "X" in the case that the peeled squares were observed.

TABLE 2

| | | Inventive Example 2-1 | Inventive Example 2 -2 | Inventive Example 2-3 | Inventive Example 2-4 | Comparative Example 2-1 | Comparative Example 2-2 |
|---|---|---|---|---|---|---|---|
| Monomer | A 1 | 20 | 45 | 65 | | | |
| (A) | A 2 | | | | 45 | | |
| | A 3 | | | | | 20 | 50 |
| Ratio (weight %) of monomer (B) contained in monomer (A) | | 0.8 | 0.8 | 0.8 | 0.4 | 6.2 | 6.2 |
| Another monomer | Butyl methacrylate | 40 | 25 | 35 | 40 | 40 | 40 |
| (C) | Styrene | 40 | 30 | | 15 | 40 | 10 |
| Mw | | 51,600 | 36,100 | 13,500 | 37,900 | 167,200 | Gellation |
| Ratio of viscosities | | ◎ | ○ | ○ | ○ | Δ | X |
| Physical properties of | Pencil hardness | H | 2 H | 2 H | H | HB | — |
| hardened film | Adhesion | ○ | ○ | ○ | ○ | ○ | — |

As can be seen from table 2, according to the polymer of the present invention, the increase of the viscosity over time was suppressed and the hardness and adhesion of the hardened film were high.

Contrary to this, according to the polymer of the comparative example 2-1, the increase of the viscosity over time was large and the pencil hardness was low. Further, the polymer of the comparative example 2-2 was gelled so that the hardened film could not be formed.

The invention claimed is:

1. A method of producing a polymer, the method comprising a step of subjecting a monomer mixture to radical polymerization, said monomer mixture comprising a cyclocarbonate group-containing (meth)acrylate monomer (A) represented by the following formula (1) and di(meth)acrylate monomer (B) represented by the following formula (2), wherein a content of said di(meth)acrylate monomer (B) contained in said monomer mixture is 3 mass % or lower and 0.1 mass % or higher, with respect to a total of a content of said monomer (A) and said content of said monomer (B), (1)

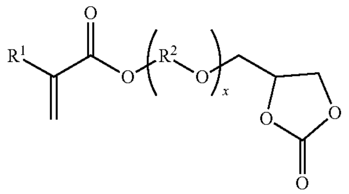

wherein in the formula (1), $R^1$ represents a hydrogen atom or a methyl group, $R^2$ represents an alkyl group having 2 to 10 carbon atoms, and X is 0 or 1, (2)

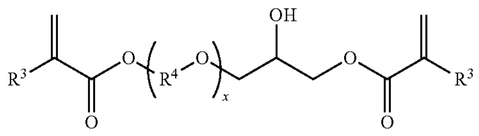

wherein in the formula (2), $R^3$ represents a hydrogen atom or a methyl group, $R^4$ represents an alkyl group having 2 to 10 carbon atoms, and X is 0 or 1.

2. The method of claim 1, wherein said content of said di(meth)acrylate monomer (B) is 0.3 mass % or higher.

3. The method of claim 1, wherein said content of said di(meth)acrylate monomer (B) is 1.5 mass % or lower.

4. The method of claim 1, further comprising a step of blowing carbon dioxide at a pressure of 0.05 to 0.3 MPa onto glycidyl methacrylate to produce said cyclocarbonate group-containing (meth)acrylate monomer (A).

5. The method of claim 1, wherein $R^1$ represents a methyl group and X is 0 in the formula (1), and wherein $R^3$ represents a methyl group and X is 0 in the formula (2).

* * * * *